(12) United States Patent
Lerner et al.

(10) Patent No.: US 8,852,569 B2
(45) Date of Patent: Oct. 7, 2014

(54) PREVENTION AND TREATMENT OF ITCH WITH CYSTEINE PROTEASE INHIBITION

(75) Inventors: Ethan Lerner, Chestnut Hill, MA (US); Vemuri B. Reddy, Ashland, MA (US)

(73) Assignee: The General Hospital Corporation, Boston, MA (US)

( * ) Notice: Subject to any disclaimer, the term of this patent is extended or adjusted under 35 U.S.C. 154(b) by 79 days.

(21) Appl. No.: 13/061,188

(22) PCT Filed: Aug. 28, 2009

(86) PCT No.: PCT/US2009/055273
§ 371 (c)(1),
(2), (4) Date: Apr. 11, 2011

(87) PCT Pub. No.: WO2010/025314
PCT Pub. Date: Mar. 4, 2010

(65) Prior Publication Data
US 2011/0184016 A1    Jul. 28, 2011

Related U.S. Application Data

(60) Provisional application No. 61/092,571, filed on Aug. 28, 2008.

(51) Int. Cl.
*A61K 31/00* (2006.01)
*A61K 31/437* (2006.01)

(52) U.S. Cl.
CPC ............ *A61K 31/00* (2013.01); *A61K 31/437* (2013.01)
USPC ....................................................... 424/78.3

(58) Field of Classification Search
CPC .................................................. A61K 31/00
USPC ....................................................... 424/78.3
See application file for complete search history.

(56) References Cited

U.S. PATENT DOCUMENTS

| | | | |
|---|---|---|---|
| 5,008,242 | A | 4/1991 | Lezdey et al. |
| 5,114,917 | A | 5/1992 | Lezdey et al. |
| 5,290,762 | A | 3/1994 | Lezdey et al. |
| 6,583,155 | B2 | 6/2003 | Butler et al. |
| 6,723,354 | B1 | 4/2004 | Ruseler-van Embden et al. |
| 6,936,606 | B2 | 8/2005 | Bekkali et al. |
| 7,312,211 | B2 | 12/2007 | Bekkali et al. |
| 2002/0035108 | A1 | 3/2002 | Gu et al. |
| 2002/0055497 | A1 | 5/2002 | Butler et al. |
| 2003/0069240 | A1 | 4/2003 | Breitenbucher et al. |
| 2007/0117785 | A1 | 5/2007 | Butler et al. |

FOREIGN PATENT DOCUMENTS

| | | |
|---|---|---|
| WO | 2008028301 A1 | 3/2008 |
| WO | 2008086069 A1 | 7/2008 |

OTHER PUBLICATIONS

Conus S, Simon Hu. Cathepsins: key modulators of cell death and inflammatory responses. Biochem Pharmacol. Dec. 1, 2008;76(11):1374-1382. Epub Aug. 12, 2008.*
Reddy et al "Cowhage evoked itch is mediated by a novel cysteine protease—a ligand of protease activated receptors", the Journal of Neuroscience, vol. 28(17), pp. 4331-4335, 2008.
Thurmond et al, "Identification of a Potent and Selective Noncovalent Cathepsin S Inhibitor", The J. of Pharmacology and Experimental Therapeutics, vol. 308, No. 1, pp. 268-276, 2004.
Biro et al., Experimental Dermatology, 14:225-240 (2005). "How best to fight that nasty itch—from new insights into the neuroimmunological, neuroendocrine, and neurophysiological bases of pruritus to novel therapeutic approaches.".
Desai et al., European Journal of Pharmacology, 538:168-174 (2006). "An orally active reversible inhibitor of cathepsin S inhibits human trans vivo delayed-type hypersensitivity."
Kutsukake et al., PNAS, 101(31):11338-11343 (2004). "Venomous protease of aphid soldier for colony defense.".
Wei et al., Bioorganic & Medicinal Chemistry Letters, 17:5525-5528 (2007). "Pyrazole-based cathepsin S inhibitors with improved cellular potency."
Grice et al., Bioorganic & Medicinal Chemistry Letters, 16:2209-2212 (2006). "The SAR of 4-substituted (6,6-bicyclic) piperidine cathepsin S inhibitors."
Palermo et al., Trends in Pharmacological Sciences, 29(1):22-28 (2007). "Cysteine cathepsin proteases as pharmacological targets in cancer."
Steinhoff et al., The Journal of Neuroscience, 23(15):6176-6180 (2003). "Proteinase-activated receptor-2 mediates itch: a novel pathway for pruritus in human skin."
Herndon, Int. J. Derm., 14:465-484 (1975). "Itching: the pathophysiology of pruritus.".
Ikoma et al., Nature Reviews Neurosci., 7, 535-547 (2006). "The neurobiology of itch."
Johanek et al., J. Neurosci., 28:7659-7669 (2008). "A role for polymodal C-fiber afferents in nonhistaminergic itch."
Namer et al., J. Neurophysiol., 100:2062-2069 (2008). "Separate peripheral pathways for pruritus in man."
Summerfield et al., Br. J. Dermatol., 105:725-6 (1981). "Pain, itch and endorphins."
Twycross et al., Q J Med, 96:7-26 (2003). "Itch: scratching more than the surface."
Winkelmann, Med. Clins. N. Am., 66:1119-1133 (1982). "Pharmacologic control of pruritus."

* cited by examiner

*Primary Examiner* — Paul Zarek
(74) *Attorney, Agent, or Firm* — David S. Resnick; Nixon Peabody LLP (57) ABSTRACT

Embodiments of the invention relates to methods of preventing itch in a subject using an therapeutically effective amount of a cysteine protease inhibitor. The itch is not associated with psoriasis and atopic dermatitis. The itch is also a non-histamine mediated itch. The cysteine protease inhibitor is an inhibitor directed to cathepsin S.

6 Claims, 2 Drawing Sheets

PREVENTION AND TREATMENT OF ITCH WITH CYSTEINE PROTEASE INHIBITION

CROSS REFERENCE TO RELATED APPLICATIONS

The application is a 35 U.S.C. §371 National Phase Entry application of International Application No. PCT/US2009/055273 filed on Aug. 28, 2009, which designates the United States, and which claims benefit of priority under 35 U.S.C. §119(e) of the U.S. Provisional Patent Application No. 61/092,571 filed on Aug. 28, 2008, the contents of which are incorporated herein by reference their entirety.

BACKGROUND OF INVENTION

Itch, or pruritus, is the unpleasant sensation that leads to a desire to scratch and is a common and distressing symptom in a variety of conditions and diseases. Itch also typically occurs in peripheral diseases such as allergic conjunctivitis, allergic rhinitis, hemorrhoids, and dermatoses of fungal, allergic and non-allergic origin, and in various inflammation-related diseases and disorders. Itching can also be a major symptom of many systemic diseases such as, Hodgkin's disease, chronic renal failure, polycythema vera, hyperthyroidism and cholestasis (see, for example, Herndon, J. H. Jr., Int. J. Derm. 14:465-484 (1975); Winkelmann, R. K., Med. Clins. N. Am. 66:1119-1133 (1982). In addition, senile itch is without an obvious cause, except perhaps xerosis, occurs in more than half of the population aged 70 years (Twycross et al., QJM. 2003, 96:7-26). In all cases chronic severe generalized itch can be disabling.

The sensation of itch is mediated by two distinct non-overlapping populations of cutaneous nerve fibers that evoke comparable degrees of itch (B. Namer et al., J. Neurophysiol. 100:2062-2069 (2008); L. M. Johanek et al., J. Neurosci. 28:7659-7669 (2008)). One set of fibers, the mechano-insensitive population, is more responsive to histamine than to cowhage. The other set is mechanosensitive and is more responsive to cowhage than to histamine (B. Namer et al.; L. M. Johanek et al., supra). Histamine is a classical mediator of itch and is associated with a wheal and flare. Since most clinical itches do not have a wheal or flare and do not respond to antihistamines, histamine is not thought to contribute to most itches (A. Ikoma et al., Nature Reviews Neurosci. 7, 535-547 (2006)). Cowhage refers to a tropical legume or, in this case, the loose hairs that cover the pods of *Mucuna pruriens*, and cowhage evoke itch. The active component of cowhage is mucunain, a cysteine protease that serves as a ligand for protease-activated receptors (PARs) 2 and 4 (V. B. Reddy et al., J. Neurosci. 28:4331-4335 (2008)).

Currently the standard treatment for itch is the administration of anti-histamines. However, not all forms of itch are responsive to anti-histamines. For example, cholestasis is characterized by generalized itch, which is not responsive to H1-antihistamines, indicating that histamine is probably not the major mediator involved. Approximately 25% of patients with uremia (chronic renal failure) suffer from severe itch unresponsive to H1-antihistamines or dialysis. However since histamine was believed to be the primary mediator of the itch sensation, conventional itch therapy involves H1-antihistamines as a first-line medication although antihistamines have no general anti-pruritic effect, and in many instances they are either ineffective or only partially effective.

Itching can be elicited by chemical, electrical, mechanical and thermal stimulation. So far no morphological structure has been identified as a specific receptor for the itch sensation, but it is assumed that itch receptors are linked to the free nerve endings of C-fibers close to the dermo-epidermal junction. The impulses set up in the thin, non-myelinated, slowly conducting C-fibers enter the spinal cord via the dorsal horn, then ascend in the contralateral spinothalmic tract, pass via the thalamus and end in the somatosensory cortex of the post-central gyrus. Itching and pain are related phenomena, and it was previously believed that itching was equal to sub-threshold pain, i.e. with increased activity in the C-fibers the perceived sensation changed from itching to pain. Although itch was once thought to be a subliminal form of pain (intensity theory), current evidence points to separate sensory neuronal systems mediating the two modalities. First, pain and itch are dissociable. Pain and itch evoke different motor responses, scratching for itch and withdrawal for pain. Second, based on clinical observations, systemically-administered opioids have a dichotomous effect on these two sensory modalities. μ-opioid receptor agonists reduce pain but can cause itch. Furthermore, antagonizing the central μ-opioid receptors, for example with naloxone or naltrexone, suppresses pruritus and at the same time may lower the pain threshold (Summerfield et al. Br. J. Dermatol. 1981, 105:725-6).

Clearly among all the topical and systemic agents that suppress itching in selected clinical settings there is no universally effective anti-pruritic drug. There is an urgent need for therapeutic agents for itch that do not target the histamine pathway. Such therapeutic agents would target non-histamine mediated itch.

SUMMARY OF THE INVENTION

Embodiments the invention are based on the discovery that a cysteine protease, cathepsin S, stimulates the activation of the PAR 2 and the PAR 4 receptors. This cathepsin S evokes itch in human subjects and is present in the epidermis of skin lesions associated with pruritic dermatoses. The PAR2 receptor has previously been implicated in mediating the itch sensation. The PAR4 receptor is similar to the PAR2 receptor and is thus implicated in mediating the itch sensation. Inhibition of cathepsin S and perhaps other cathepsins can inhibit the activation of these itch receptors, PAR 2 and 4. Therefore, inhibitors of cathepsin S and other cathepsins can be used for preventing and/or treating itch. Accordingly, the invention described herein provides a method of preventing itch in a subject in need thereof, comprising administering to the subject a therapeutically effective amount of a cysteine protease inhibitor.

In another embodiment, the invention described herein also provides a method of treating itch in a subject in need thereof, comprising administering to the subject a therapeutically effective amount of a cysteine protease inhibitor, wherein the itch is not associated with psoriasis and atopic dermatitis.

In one embodiment, the itch is a non-histamine mediated itch. As used herein, a "non-histamine mediated itch" refers to an itch sensation that is not alleviated by antihistamines and is not elicited via histaminergic pathway.

The subject is any mammal that expresses the PAR receptors, such as a human, a dog, a cat, and a horse.

In one embodiment, the cysteine protease used in the methods of preventing and/or treating itch is a cathepsin.

In one embodiment, the cathepsin is selected from the group consisting of cathepsin B, C, F, J, K, H, L, P, Q, S, W, X, V, and Z. In another embodiment, the cysteine protease inhibitor is selected from the group as set forth in Table I.

In one embodiment, the method is used for preventing itch associated with a disease or disorder selected from eczema, atopic eczematous dermatitis, seborrheic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

In one embodiment, the method is used for treating itch associated with a disease or disorder selected from eczema, atopic eczematous dermatitis, seborrheic dermatitis, contact dermatitis, irritant dermatitis, xerosis (dry skin), fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

In another embodiment, the methods described herein are also applicable to itch with no known etiology.

In one embodiment, the inhibitors can be administered in conjunction with other medicaments associated with the respective medical condition. Examples include menthol and phenol, calamine, topical antihistamines, local anesthetics, capsaicin, strontium nitrate, H1-receptor antagonists, H2-receptor antagonists, H4-receptor antagonists, doxepin, ondansetron, paroxetine, and mirtazapine. Other medicaments include but are not limited to, for dry skin: emollient cream; for cholestasis: colestyramine, rifampicin, opioid antagonists, androgens; for uremia: dialysis, UVB phototherapy and for paraneoplasia: paroxetine.

DETAILED DESCRIPTION OF THE INVENTION

Unless otherwise explained, all technical and scientific terms used herein have the same meaning as commonly understood by one of ordinary skill in the art to which this disclosure belongs. Definitions of common terms in medicine, dermatology, cell and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Methods in Enzymology: Guide to Molecular Cloning Techniques Vol. 152, S. L. Berger and A. R. Kimmerl Eds., Academic Press Inc., San Diego, USA (1987)); Current Protocols in Molecular Biology (CPMB) (Fred M. Ausubel, et al. ed., John Wiley and Sons, Inc.); Current Protocols in Protein Science (CPPS) (John E. Coligan, et. al., ed., John Wiley and Sons, Inc.); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The singular terms "a," "an," and "the" include plural references unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DEFINITIONS OF TERMS

As used herein, the term "itch", technically known as pruritus refers to the sensation that elicits a reflex response to scratch. Itch can be a symptom of a disease, disorder or infection, or itch can arise spontaneously, without an underlying or identifiable physiological cause, known as idiopathic pruritus.

As used herein, the term "treatment" refers to all aspects of control of itching including therapy. Control of itch includes reducing, alleviating, relieving and numbing the sensation of itch. Control of itch also includes reducing the desire to scratch.

As used herein, the term "prevent" or "prevention" refers to stopping, hindering, and/or slowing down the onset of itch sensations and symptoms, wherein the itch sensations and symptom can be associated with medical conditions or have no known etiology.

As used herein, the term "therapeutically effective amount" and grammatical variations thereof refer to sufficient quantities of the active compound that can produce the desired therapeutic effect when administered to a mammal afflicted with pruritus. The term "therapeutic effect" is used herein in a broad sense and includes prophylactic effects. Desired therapeutic effects includes but not limited to reduced sensation of itch, distraction due to the itch sensation and the desire to scratch.

As used herein, the term "antagonist" in "a PAR2 antagonist" or "PAR4 antagonist" refers to any organic or inorganic molecule that opposes the naturally occurring signaling events elicited by protease-activated receptor protein respectively. For example, an antibody that blocks the interaction of a protease and PAR protein, and thereby preventing the cleavage-activation of the PAR signaling pathway.

As used herein, the term "comprising" means that other elements can also be present in addition to the defined elements presented. The use of "comprising" indicates inclusion rather than limitation.

As used herein, a "non-histamine mediated itch" refers to an itch sensation that is not alleviated by antihistamines and is not elicited via histaminergic pathway.

Embodiments of the present invention is based on the discovery that an activity of a cysteine protease on the G-protein coupled protease activated receptor 2 (PAR2) or protease activated receptor 4 (PAR4) results in the itch sensation. The cysteine protease that elicited the itch sensation was isolated and identified from the plant *Mucuna pruriens*, also known as cowhage, is referred to as mucunain. Mucunain activation of PAR2 or PAR4 induces an influx of calcium into the transfect cells expressing the PAR4 protein, and elicited a signal transduction event that led to the sensation of itch. The inventors tested other cysteine proteases that occur naturally in animals, evaluated their activities on the PAR 2 and 4 proteins, and evaluated the related signal transduction events elicited from these cleaved PAR proteins. The inventors found that a cysteine protease, cathepsin S, was able to elicit similar calcium influx and signaling events in transfected cells expressing PAR 2 and 4 proteins.

Accordingly, cysteine proteases represent targets for the prevention, inhibiting, and/or treatment of itch, such as, the inhibition of cysteine proteases activity and the inhibition of the expression of the cysteine proteases. Preferably, the target cysteine proteases are the endogenous cysteine proteases which occur naturally in a subject afflicted by itch, and more preferably, those cysteine proteases which occur naturally with and are expressed with PAR proteins, such as, with PAR 2 and PAR 4.

In other embodiments, exogenous cysteine proteases can also be targeted. Exogenous cysteine proteases include but are not limited to those associated with parasites that itch such as hookworm and schistosomiasis as well as those associated with *Malassezia* or *Pityrosporum* yeasts implicated in itchy scalp.

Accordingly, in one embodiment, the present inventions provide a method of preventing itch in a subject in need thereof, the method comprises administering a therapeutically effective amount of a cysteine protease inhibitor. In one embodiment, the cysteine protease that is to be inhibited is a cathepsin and is selected from the group consisting of cathepsin C, F, J, K, H, L, P, Q, S, W, X, V, and Z. In one embodiment, the itch to be prevented is associated with seborrheic dermatitis, xerosis, eczema, atopic eczematous dermatitis, seasonal allergy and summer seasonal recurrent dermatitis (also known as summer eczema and sweet itch). These itchy conditions are seasonal, occurring at approximately the same periods within a year. Knowing that the seasons or months that these itchy conditions are bound to occur, prophylactic measures can be taken to prevent the onset of itchy symptoms and also to lessen the severity of the itchy symptoms.

Accordingly, in one embodiment, the present inventions provide a method of treating itch in a subject in need thereof, the method comprises administering a therapeutically effective amount of a cysteine protease inhibitor, wherein the itch is not associated with psoriasis and atopic dermatitis. In one embodiment, the cysteine protease that is to be inhibited is a cathepsin and is selected from the group consisting of cathepsin C, F, J, K, H, L, P, Q, S, W, X, V, and Z.

In one embodiment, the itch is a non-histamine mediated itch. As used herein, a "non-histamine mediated itch" refers to an itch sensation that are not alleviated by antihistamines and is not elicited via histaminergic pathway.

Itch or pruritus is defined as an unpleasant sensation that evokes the desire or reflex to scratch. Itches are a common problem and can be localized (limited to one area of the body) or generalized (occurring all over the body or in several different areas). The medical term for itching is pruritus. Generalized itch, for obvious reasons, is more difficult to treat than localized itch. Itches can also occur with or without skin lesions (for example, papules, nodules or blisters).

Itch can originate in the peripheral nervous system (dermal or neuropathic) or in the central nervous system (neuropathic, neurogenic, or psychogenic). Itch originating in the skin is considered pruritoceptive and can be induced by a variety of stimuli, including mechanical, chemical, thermal, and electrical stimulation. The primary afferent neurons responsible for histamine induced itch are unmyelinated C-fibers. In human C-fiber nociceptors, two major classes exist: mechano-responsive nociceptors and mechano-insensitive nociceptors. Mechano-responsive nociceptors have been shown in studies to respond to mostly pain and mechano-insensitive receptors respond mostly to itch induced by histamine. The feeling of itchiness can be caused by a movement of hair or the release of a chemical (histamine) from cells under the skin. Itchiness is regarded as protective when it helps creatures remove parasites that land on their skin.

Neuropathic itch can originate at any point along the afferent pathway as a result of damage of the nervous system. They could include diseases or disorders in the central nervous system or peripheral nervous system. Examples of neuropathic itch in origin are nostalgia paresthetica, brachioradial pruritus, brain tumors, multiple sclerosis, peripheral neuropathy, and nerve irritation.

Neurogenic itch, which is itch induced centrally but with no neural damage, is often associated with increased accumulation of endogenous opioids and possibly synthetic opioids.

Itch is also associated with some psychiatric disorders such as delusions of parasitosis or related obsessive-compulsive disorders, for example neurotic scratching or skin picking.

Itching can be caused by many other conditions. For example, xerosis, is a common cause, frequently seen in winters. It is associated with older age, frequent bathing in hot showers or baths, and high temperature and low humidity environments. Skin conditions (such as psoriasis, eczema, sunburn, athlete's foot, hidradenitis suppurativa and many others) are also other common causes. Most are of an inflammatory nature. Other causes include but are not limited to: insect bites, such as those from mosquitoes, fleas or chiggers; allergic reactions to contact with specific chemicals, such as urushiol from poison ivy or poison oak; cancers of the blood such as Hodgkin's disease; jaundice where the built up of bilirubin is a skin irritant at high concentrations; polycythemia, which can cause generalized itching due to increased histamine; scabies or infection with lice or worms; liver, kidney, and thyroid illnesses; shaving, which can irritate the skin; diabetes mellitus; dandruff where there is an unusually large amount of epidermal flaking associated with this sensation; iron deficiency such as anemia; parasitic infections such as certain parasites of birds and mammals that are released from infected snails in fresh and saltwater and they cause swimmer's itch, also called cercarial dermatitis; allergy to psychiatric medication; fungal infections, e.g. of the crotch (tinea cruris) commonly known as jock itch, as well as vaginal itching and/or anal itching from sexually transmitted diseases (STDs) or other types of infections; photodermatitis—sunlight reacts with chemicals in the skin, leading to the formation of irritant metabolites, for example, sunburn; directly contact or ingestion of chemical compounds or drugs, e.g. morphine and other opiates; cholestasis related to pregnancy: pruritic urticarial papules and plaques of pregnancy (PUPPP); and gestational pemphigoid. Causes of itch can also be psychological, that is, due to stress, anxiety, etc., and stress also can aggravate itch from other causes.

Accordingly, itch can be associated with a disease or disorder selected from eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with liver, kidney disease, and hyperthyroidism; itch associated with haemodialysis, burns, scalds, sunburn, wound healing, insect bites, urticaria, sweat gland abnormalities, bullous pemphigoid, photodematoses, skin blisters, adult acne, chicken pox, and dermatitis herpetiformis.

Itching usually prompts scratching, which can sometimes lead to a vicious itch-scratch cycle. Scratching can initially feel satisfying, but prolonged scratching just leaves one with irritated skin that can still itch and often causes itching itself. Since scratching provides only temporary relief and does not promote healing of the underlying problem, it is best to avoid scratching if at all possible. If scratching breaks open the skin, bacterial infection can set in. And if scratching continues for many months or years, the area that is scratched may develop thickened skin (lichenification) or pigmentation that darkens the area. Obviously, the best way to allow irritated skin to heal is to stop scratching it. However, will power often is not enough since the urge to scratch can be compelling.

Cathepsins belong to the papain superfamily of cysteine proteases. These proteases function in the normal physiological as well as pathological degradation of connective tissue. Cathepsins play a major role in intracellular protein degradation, turnover and remodeling. To date, a number of cathepsin have been identified and sequenced from a number of sources. These cathepsins are naturally found in a wide variety of tissues (see review by Barrett and Kirschke, Methods Enzymol. 1981, 80 Pt C:535-61). For example, cathepsin B, F, H, L, K, S, W, and Z have been cloned. Cathepsin K (which is also known by the abbreviation cat K) is also known as cathepsin O and cathepsin O2. See U.S. Pat. No. 5,861,298, which is hereby incorporated by reference in its entirety. Cathepsin L is implicated in normal lysosomal proteolysis as well as several disease states, including, but not limited to, metastasis of melanomas. Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, J. Biol. Chem. 272:13955-13960; Littlewood-Evans, A. et al., 1997, Bone 20:81-86, which are hereby incorporated by reference in their entirety.

Cathepsin S is one of the major cysteine proteases, and is expressed in the lysosome of antigen presenting cells; primarily dendritic cells, B-cells and macrophages. Cathepsin S is most well known for its critical function in the proteolytic digestion of the invariant chain chaperone molecules, thus controlling antigen presentation to CD4+ T-cells by major histocompatibility complex (MHC) class II molecules or to NK1.1+ T-cells via CD1 molecules. Cathepsin S also appears to participate in direct processing of exogenous antigens for presentation by MHC class II to CD4+ T-cells, or in cross-presentation by MHC class I molecules to CD8+ T-cells. The protease is necessary for removal of the invariant chain in the peptide binding region of the class II protein before the antigen peptide can be bound and presented to T cells (Villadangos J A, et al., Immunol. Rev. 1999, 172:109-20). In addition, cathepsin S is also implicated in arterial remodeling and atherogenesis. In human atherosclerotic lesions, there is overespression of cathepsin S (Liu J. et. al., Arterioscler. Thromb.

Vasc. Biol. 2004, 24:1359-66). Cathepsin S appears to be involved in degradation of the extracellular matrix, which may then contribute to the pathology of a number of diseases, including arthritis, atherosclerosis and chronic obstructive pulmonary disease. Thus, inhibitors of cathepsin S are postulated as a potential therapeutic target for the treatment of rheumatoid arthritis, psoriasis, multiple sclerosis and other autoimmune-based inflammatory diseases. Recently, cathepsin S gene expression was shown to be strongly correlated with subjects' body mass index (BMI). This suggests a role of cathepsin S in obesity and atherosclerosis, and that cathepsin S can be a potential therapeutic target to reduce associated cardiovascular risks in obese patients (Taleb and Clement, Clin. Chem. Lab. Med. 2007, 45:328-32). In support of this, there is a report of cathepsin S release from adipocytes (Marcus and Stern, J. Cardiometab. Syndr. 2006, 1(2):121-4). Cathepsin S is also implicated in Alzheimer's disease and certain autoimmune disorders, including, but not limited to juvenile onset diabetes, multiple sclerosis, pemphigus vulgaris, Graves' disease, myasthenia gravis, systemic lupus erythematosus, rheumatoid arthritis, Hashimoto's thyroiditis; allergic disorders, including, but not limited to asthma; and allogeneic immune responses, including, but not limited to, rejection of organ transplants or tissue grafts.

Cathepsin K is most closely related to cathepsin S having 56% sequence identity at the amino acid level. The S 2 P 2 substrate specificity of cathepsin K is similar to that of cathepsin S with a preference in the P1 and P2 positions for a positively charged residue such as arginine, and a hydrophobic residue such as phenylalanine or leucine, respectively. See Bromme, D. et al., 1996 J Biol. Chem., 271: 2126-2132; Bossard, M. J. et al., 1996, J Biol. Chem., 271:12517-12524, which are hereby incorporated by reference in their entirety. Cathepsin K is active at a broad pH range with significant activity between pH 4-8, thus allowing for good catalytic activity in the resorption lacunae of osteoclasts where the pH is about 4-5.

There are fifteen human cathepsins, including eleven cysteine, two aspartic and two serine proteases. Cathepsins were traditionally considered lysosomal proteases. It is now recognized that the broad expression and range of pH dependence of some cathepsins reveal that they have many functional roles including tissue remodeling, metastasis and inflammation. Examples of cysteine cathepsin activities include cleavage of collagen by cathepsin L to generate endostatin, an endogenous inhibitor of angiogenesis, and cleavage of the invariant chain in antigen presenting cells by cathepsin S as part of the inflammatory cascade.

There are four PARs and they are members of the G-protein coupled receptor family. Their identified endogenous ligands are all serine proteases, including thrombin, the ligand for PAR 1. The presence of PAR2 on free nerve endings in the skin and keratinocytes and PAR2 and PAR4 on dorsal root ganglia link these receptors to itch and pain (G. Schwarz et al., J. Invest. Dermatol. 119:44-49 (2002)).

In one embodiment, the method of treating and/or preventing itch in a subject, the method comprises administering therapeutically effective amount of a cysteine protease inhibitor. In one embodiment, the cysteine protease inhibitor is a cathepsin inhibitor. While not wishing to be bound by theory, inhibition of a cysteine protease that can activate the PAR 2 and 4 protein receptors (i.e. the "itch' receptors) by protein cleavage can stop and/or reduce and also prevent the signaling events elicited from these PAR proteins and consequently the itch sensation the subject will experience. Inhibitors of cathepsin can be any organic or inorganic compound or agent that binds to the substrate-binding site of the enzyme cathepsin and prevents the interaction of cathepsin with PAR proteins. For example, peptides of PAR 2 or 4 that bind the substrate-binding site of a cathepsin. Such peptides function as decoy ligands, occupying all available substrate-binding site, so there will be no or fewer unoccupied cathepsin to activate the PAR proteins. Alternatively, a molecule that mimics the peptide, sequence, or binding motif of PAR protein that fits into the substrate-binding site of the enzyme cathepsin. Inhibitors of cathepsin can also be any organic or inorganic compound or agent that binds to other regions of the enzyme cathepsin and cause a structural conformational change in the enzyme such that the enzyme cannot bind its substrate, PAR proteins, or if successfully PAR proteins-binding occurs, the enzyme cannot execute the peptide bond cleavage reaction. Cathepsin inhibitors can be reversible, i.e. the enzyme cathepsin will resume to full protease activity when that inhibitor is removed; or irreversible, i.e. the inhibitor binds with such great affinity that its removal is not possible. As such, the enzyme is permanently inhibited.

The use of cysteine protease inhibitors as anti-pruritics is advantageous in that they relieve itching by a mechanism independent of anti-histaminergic compounds. Thus, they can be effective in itch-related diseases which are refractory to antihistamine therapy and can be combined with H1-antihistamines to provide superior therapy via additive or synergistic interaction.

In one embodiment, the cathepsin inhibitor is selected from the group consisting of stefin A, stefin B, cystatin C, human testican-1, naphthalene endoperoxide (effective against Cathepsin B, L, S), CA-074 (specific for cathepsin B), odanacatib (formerly MK-0822) (specific for cathepsin K), CLIK-148 and CLIK-195 (specific for cathepsin L), CLIK-60 (specific for cathepsin S), fluoromethyl ketone, heterocyclic oxygen-containing peptidomimetics, vinyl sulfones, pyridoxal phosphate, high potent pyrazole-based compounds such as 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine (aka JNJ 10329670), RWJ-445380, and compounds 1-41 of Johnson & Johnson Pharmaceutical as described by Wei, J. et al. (Bioorganic & Medicinal Chemistry Letters, 2007, 17:5525-5528) and in R. L. Thurmond, et al. J. Pharmaco. Exp. Therapeutics, 2004, 268-276; Compounds I, II, and III, from Boehringer Ingelheim Pharmaceuticals (Desai, S, N. et. al., Eur. J. Pharmacol. 538: 168-174); leupeptin, and chloroquine. These references are hereby incorporated by reference in their entirety.

In another embodiment, the cathepsin inhibitor is selected from those described in the U.S. Pat. Nos. 5,374,623; 5,317,086; 5,776,718; 5,998,470; 6,004,933; 6,048,861; 6,057,362; 6,232,342; 6,284,777; 6,353,017; 6,369,077; 6,331,1542; 6,420,364; 6,455,502; 6,476,026; 6,462,076; 6,492,362; 6,506,733; 6,566,373; 6,576,630; 6,583,137; 6,583,155; 6,635,621; 6,835,727; 6,876,706; 6,953,793; 6,936,606; 7,279,478; 7,312,211; U.S. Pat. Applications 2003/0069240 and 2007/0117785; and the PCT application WO/2005/066159, and these are hereby incorporated by reference in their entirety.

In one embodiment, the cysteine protease inhibitor is a non-specific inhibitor. For example, E-64 (trans-epoxysuccinyl-L-leucylamide-(4-guanidino) butane).

In one embodiment, the cathepsin inhibitor is a specific inhibitor, for example, specific inhibitors for cathepsin K, S, or L. Selective peptide based inhibitors of cathepsin K have been developed See Bromme, D., et al., 1996, Biochem. J. 315:85-89; Thompson, S. K., et al., 1997, Proc. Natl. Acad. Sci. USA. 94:14249-14254, which are hereby incorporated by reference in their entirety. The crystal structure of cathepsin K has been resolved. See McGrath, M. E., et al., 1997, Nat. Struct. Biol. 4:105-109; Zhao, B., et al., 1997, Nat. Struct. Biol. 4: 109-11, which are hereby incorporated by reference in their entirety. Using the crystal structures and aided by computer modeling programs, synthetic organic compounds that mimic the substrate-binding site of cathepsin K can be designed. Such software for computer assisted molecular (Drug) design can be found at the World Wide Web "period" netsci "period" org/Resources/Software/Modeling/CADD/, e.g. MOLSCAT, Chem3D, and ADAPT. Examples of specific cathepsin inhibitors include naphthalene endoperoxide—singlet oxygen. Singlet oxygen is a causal factor in light-induced skin photoaging and the cytotoxic process of tumor cells in photodynamic chemotherapy. Naphthalene endoperoxide is specific for cathepsins B, L, and S.

In one embodiment, the cathepsin inhibitor is a specific inhibitor for cathepsin S.

In one embodiment, the cathepsin inhibitor is RWJ-445380 or derivatives thereof.

In one embodiment, the cathepsin inhibitor is 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine (aka JNJ 10329670) or derivatives thereof.

Envisioned herein are the derivatives of cysteine protease inhibitors and cathepsin inhibitors. Derivatives, as used herein, include a chemically modified compound wherein the modification is considered routine by the ordinary skilled chemist, such as additional chemical moieties (e.g., an ester or an amide of an acid, protecting groups, such as a benzyl group for an alcohol or thiol, and tert-butoxycarbonyl group for an amine). Derivatives also include radioactively labeled cysteine protease inhibitors and cathepsin inhibitors, conjugates of cysteine protease inhibitors and cathepsin inhibitors (e.g., biotin or avidin, with enzymes such as horseradish peroxidase and the like, with bioluminescent agents, chemoluminescent agents or fluorescent agents). Additionally, moieties can be added to the cysteine protease inhibitors and cathepsin inhibitors or a portion thereof to increase half-life in vivo. Derivatives, as used herein, also encompasses analogs, such as a compound that comprises a chemically modified form of a specific compound or class thereof, and that maintains the pharmaceutical and/or pharmacological activities characteristic of said compound or class, are also encompassed in the present invention. Derivatives, as used herein, also encompasses prodrugs of the cysteine protease inhibitors and cathepsin inhibitors, which are known to enhance numerous desirable qualities of pharmaceuticals (e.g., solubility, bioavailability, manufacturing, etc.).

In one embodiment, the method described herein is applicable to preventing itch that is associated with seasonal conditions such as seborrheic dermatitis, xerosis, eczema, and atopic eczematous dermatitis. Subjects that have previous episodes of these conditions but currently the symptoms have disappeared. Such subjects are highly susceptible to itch when these conditions do occur again, For example, xerosis is common among the elderly living in temperate climates mainly during the winter months because of the enclosed indoor heating and low humidity during the winter months. Pruritus can also develop as a result of disruption of the epidermal barrier associated with aging leading to inflammation and the release of cysteine proteases, activation of PARs and then the sensation of itch. Similarly, eczema, and atopic eczematous dermatitis tend to "flare up" when there is low humidity and/or during the winter months. Atopic dermatitis is also associated with altered skin barrier function, inflammation and the release of cysteine proteases, activation of PARs and then the sensation of itch. Other examples of seasonal itch include but are not limited to the itch associated with seasonal allergy (also known as hay fever) during the autumn and spring each year. Dogs and horses are known to suffer from seasonal itch in the fall and the late spring. Summer seasonal recurrent dermatitis (SSRD), also known as summer eczema and sweet itch is a skin disease caused by allergic reaction to insect bites. SSRD is considered to be caused by an allergic reaction to the saliva of Culicoides flies (also called midges and "no-see-ums"), grass protein, and filariad worm larvae. Sweet itch occurs only in the late spring and summer when insects are present; during the winter months the skin heals and the hair grows back. The therapeutics described herein can be administered during the winter months to the elderly, administered for a subject who has eczema and is temporarily relocating to a dry climate, e.g. vacation, or administered during the seasons when seasonal itch occurs.

In another embodiment, the method described herein is used in conjunction with other known anti-itch therapies such as menthol, menthol and phenol, calamine, topical antihistamines, local anesthetics, capsaicin, strontium nitrate, H1-receptor antagonists, H2-receptor antagonists, doxepin, ondansetron, paroxetine, mirtazapine, opioid antagonists and neurontin. For example, for dry skin itch: emollient cream; for cholestasis-related itch: colestyramine, rifampicin, opioid antagonists, and androgens; for uremia-related itch: dialysis, UVB phototherapy; and for paraneoplasia-related itrch: paroxetin.

In another embodiment, the method described herein can be used in conjunction with therapies for eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, and dermatitis herpetiformis.

In some embodiment, more than one cysteine protease inhibitor is administered for the treatment of itch. Several cysteine protease inhibitors, each inhibitor for a specific cathepsin, are administered. For example, the combination of CLIK-60 (specific for cathepsin S), SB 331750 (specific for cathepsin K) and CLIK-195 (specific for cathepsin L) can be used for the treatment and/or prevention of itch. A cathespin inhibitor that is not specific for a single cathepsin may also be administered.

In one embodiment, the cysteine protease inhibitor described herein is administered in conjunction with a PAR2 antagonist, for example, the synthetic peptide FSLLRY-NH$_2$ (SEQ. ID. No. 1), the small molecule ENMD-1068: N(1)-3-methylbutyryl-N(4)-6-aminohexanoyl-piperazine, PAR2 monoclonal antibody, SAM-11 and P2pal-21 (Covic, J., et al., 2002, PNAS, 99:643-648).

In another embodiment, the cysteine protease inhibitor described herein is administered in conjunction with a PAR 4 antagonist, for example, tcY-NH(2); pepducin P4 pal-10; pepducin P4 pal-15; Tc-APGKF-NH(2) (SEQ. ID. No. 2);

polyclonal anti-PAR4 antibody; monoclonal anti-PAR4 antibody, YD-3; Statins: atorvastatin, pravastatin, fluvastatin, cerivastatin, lovastatin, simvastatin, rosuvastatin, pitavastatin, and metabolite thereof; and ethanol. Method of treating itch with a PAR 4 antagonist is described in U.S. patent application Ser. No. 11/968,800 and this is hereby incorporated by reference by its entirety.

In one embodiment, the cysteine protease inhibitor is administered as a pharmaceutical composition comprising a cysteine protease inhibitor and a pharmaceutically acceptable carrier.

Such compositions include solutions, suspensions, lotions, gels, creams, ointments, emulsions, skin patches, etc. All of these dosage forms, along with methods for their preparation, are well known in the pharmaceutical and cosmetic art. Harry's Cosmeticology (Chemical Publishing, 7th ed. 1982); Remington's Pharmaceutical Sciences (Mack Publishing Co., 18th ed. 1990). Typically, such topical formulations contain the active ingredient in a concentration range of 0.001 to 10 mg/ml, in admixture with suitable vehicles. Other desirable ingredients for use in such anti-pruritic preparations include preservatives, co-solvents, viscosity building agents, carriers, etc. Solvents includes such as propylene glycol, polyethylene glycol 300, polyethylene glycol 400 or polyethylene glycol 1540 alone or in combination with 1,2,6-hexanetriol, propylene carbonate or other such solvents. The carrier itself or a component dissolved in the carrier may have palliative or therapeutic properties of its own, including moisturizing, cleansing, or anti-inflammatory/anti-itching properties. The cysteine protease inhibitors of the method described herein can be combined with a therapeutically effective amount of anti-inflammatories such as corticosteroids, fungicides, antibiotics, moisturizers or anti-itching compounds; and PAR2 and PAR4 antagonists.

Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Topical administration of a pharmacologically effective amount may utilize transdermal delivery systems well known in the art such as those described in U.S. Pat. Nos. 4,627,429, D296,006, 4,921,475, 5,591,767, 5,681,580, 6,009,346, 6,190,315, 7,066,884 for passive, automated, iontophoretic, and sonophoretic transdermal delivery. These patents are hereby incorporated by reference in their entirety.

In addition to topical therapy, the cysteine protease inhibitors described herein can also be administered systemically in a pharmaceutical formulation. Systemic routes include but are not limited to oral, parenteral, nasal inhalation, intratracheal, intrathecal, intracranial, and intrarectal. The pharmaceutical formulation is preferably a sterile saline or lactated Ringer's solution. For therapeutic applications, the preparations described herein are administered to a mammal, preferably a human, in a pharmaceutically acceptable dosage form, including those that may be administered to a human intravenously as a bolus or by continuous infusion over a period of time, by intramuscular, intraperitoneal, intracerebrospinal, subcutaneous, intra-epidermal, intra-arterial, intrasynovial, intrathecal, oral, topical, or inhalation routes. For these uses, additional conventional pharmaceutical preparations such as tablets, granules, powders, capsules, and sprays may be preferentially required. In such formulations further conventional additives such as binding-agents, wetting agents, propellants, lubricants, and stabilizers may also be required.

The compositions can be formulated as a sustained release composition. For example, sustained-release pharmaceutical compositions include, but are not limited to, sustained-release matrices such as biodegradable matrices or semi-permeable polymer matrices in the form of shaped articles, e.g., films, or mirocapsules that comprise cysteine protease inhibitors described herein.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919; EP 58,481), copolymers of L-glutamic acid and gamma-ethyl-L-glutamate (U. Sidman et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(–)-3-hydroxybutyric acid (EP 133,988). Sustained-release compositions also include liposomally entrapped cathepsin inhibitors. Such liposomes can be prepared by methods known well known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979). Other known methods are described in DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324, all of which are hereby incorporated by reference in its entirety. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474; 4,925,673 and 3,625,214, and Jein, TIPS 19:155-157 (1998), the contents of which are hereby incorporated by reference.

Preferred microparticles are those prepared from biodegradable polymers, such as polyglycolide, polylactide and copolymers thereof. Those of skill in the art can readily determine an appropriate carrier system depending on various factors, including the desired rate of drug release and the desired dosage.

In one embodiment, the formulations comprising cysteine protease inhibitors are administered via catheter directly to the inside of blood vessels. The administration can occur, for example, through holes in the catheter. In those embodiments wherein the active compounds have a relatively long half life (on the order of 1 day to a week or more), the formulations can be included in biodegradable polymeric hydrogels, such as those disclosed in U.S. Pat. No. 5,410,01. These polymeric hydrogels can be delivered to the inside of a tissue lumen and the active compounds released over time as the polymer degrades. If desirable, the polymeric hydrogels can have microparticles or liposomes which include the active compound dispersed therein, providing another mechanism for the controlled release of the active compounds.

In one embodiment, osmotic minipumps are used to provide controlled sustained delivery of pharmaceutical compositions comprising cysteine protease inhibitors described herein, through cannulae to the site of interest, e.g. directly into a tissue at the site of metastatic growth or into the vascular supply of a tumor. The pump can be surgically implanted, for example continuous administration of endostatin, an anti-angiogenesis agent, by intraperitoneally implanted osmotic pump is described in Cancer Res. 2001 Oct. 15; 61(20):7669-74. Therapeutic amounts of a cysteine protease inhibitor can also be continually administered by an external pump attached to an intravenous needle.

For enteral administration, a composition comprising cysteine protease inhibitors described herein can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature. The enteral composition can be formulated for timed, sustained release such as in beads with multi layers providing a lag time before drug release.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration may be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including EDTA, citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS(N,N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

Formulations for rectal administration may be presented as a suppository with a conventional carrier, e.g., cocoa butter or Witepsol S55 (trademark of Dynamite Nobel Chemical, Germany), for a suppository base.

When the cysteine protease inhibitors contain a basic group, pharmaceutically acceptable salts can be used. Such salts encompassed within the term "pharmaceutically acceptable salts" refer to non-toxic salts which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucaamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

In one embodiment, the cysteine protease inhibitors described herein includes within its scope prodrugs of the cysteine protease inhibitors. In general, such prodrugs will be functional derivatives of the cysteine protease inhibitors which are readily convertible in vivo into the active cysteine protease inhibitors. Thus, in the methods of treatment of the present invention, the term "administering" shall encompass the treatment of the various conditions described with the cysteine protease inhibitors specifically disclosed or with a cysteine protease inhibitors which may not be specifically disclosed, but which converts to an active cysteine protease inhibitor in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of cysteine protease inhibitors into the biological milieu.

Pharmaceutically acceptable carriers that are inherently nontoxic and nontherapeutic are preferred. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of compositions include polysaccharides such as sodium carboxymethylcellulose or methylcellulose, polyvinylpyrrolidone, polyacrylates, polyoxyethylene-polyoxypropylene-block polymers, polyethylene glycol and wood wax alcohols. For all administrations, conventional depot forms are suitably used. Such forms include, for example, microcapsules, nano-capsules, liposomes, plasters, inhalation forms, nose sprays, sublingual tablets, and sustained release preparations. For examples of sustained release compositions, see U.S. Pat. No. 3,773,919; EP 58,481A; U.S. Pat. No. 3,887,699; EP 158,277A; Canadian Patent No. 1176565; U. Sidman et al., Biopolymers 22:547 (1983) and R. Langer et al., Chem. Tech. 12:98 (1982), all of which are hereby incorporated by reference in its entirety. The cysteine protease inhibitors will usually be formulated in such vehicles at a concentration of about 0.1 mg/ml to 1000 mg/ml.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes). The cysteine protease inhibitors can be stored in lyophilized form or as an aqueous solution if it is highly stable to thermal and oxidative denaturation. The pH of the cysteine protease inhibitor preparations typically can be about from 4 to 8.

The precise dosage of a selected cysteine protease inhibitor will vary with the route of administration, the dosage form, the dosing schedule, the oral potency of the selected cysteine protease inhibitor chosen, its physicochemical characteristics, the age, size, sex and condition of the mammal or human, the nature, severity, and the location of the itch sensations and underlying disorder if any, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. The selection of proper dosage is well within the skill of an ordinary skilled physician. For example, topical formulations are usually administered up to four-times a day; an effective oral dose of a cysteine protease inhibitor is typically from about 1.5 to about 6000 µg/kg body weight and preferably about 10 to about 2000 µg/kg of body weight.

The invention can be defined by any of the following alphabetized paragraphs:

[A] The use of a cysteine protease inhibitor in the manufacture of medicament for the prevention of itch.

[B] The use of a cysteine protease inhibitor in the manufacture of medicament for the treatment of itch, wherein the itch is not associated with psoriasis and atopic dermatitis.

[C] The use of a cysteine protease inhibitor in the manufacture of medicament for the treatment of itch, wherein the itch is non-histamine mediated.

[D] The use of a cysteine protease inhibitor for the prevention of itch.

[E] The use of a cysteine protease inhibitor for the treatment of itch, wherein the itch is not associated with psoriasis and atopic dermatitis.

[F] The use of a cysteine protease inhibitor for the treatment or prevention of itch, wherein the itch is non-histamine mediated.

[G] The use of any of paragraphs [A]-[F], wherein the cysteine protease is a cathepsin.

[H] The use of paragraph [G], wherein the cathepsin is selected from the group consisting of cathepsin C, F, J, K, H, L, P, Q, S, W, X, V, and Z.

[I] The use of any of paragraphs [A]-[G], wherein the cysteine protease inhibitor is selected from the group as set forth in Table I.

[J] The use of paragraph [A], [D] or [F], wherein the itch is associated with a disease or disorder selected from eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

[K] The use of paragraph [B], [E] or [F], wherein the itch is associated with a disease or disorder selected from eczema, atopic eczematous dermatitis, seborrheic dermatitis, contact dermatitis, irritant dermatitis, xerosis (dry skin), fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

[L] A method of preventing itch in a subject in need thereof, comprising administering to the subject a therapeutically effective amount of a cysteine protease inhibitor.

[M] A method of treating itch in a subject in need thereof, comprising administering to the subject a therapeutically effective amount of a cysteine protease inhibitor, wherein the itch is not associated with psoriasis and atopic dermatitis.

[N] The method of paragraphs [L] or [M], wherein the itch is non-histamine mediated.

[O] The method of paragraphs [L] or [M], wherein the cysteine protease is a cathepsin.

[P] The method of paragraph [O], wherein the cathepsin is selected from the group consisting of cathepsin B, C, F, J, K, H, L, P, Q, S, W, X, V, and Z.

[Q] The method of paragraphs [L] or [M], wherein the cysteine protease inhibitor is selected from the group as set forth in Table I.

[R] The method of paragraph [L], wherein the itch is associated with a disease or disorder selected from eczema, atopic eczematous dermatitis, seborrheic dermatitis, atopic dermatitis, contact dermatitis, irritant dermatitis, xerosis (dry skin), psoriasis, fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

[S] The method of paragraph [M], wherein the itch is associated with a disease or disorder selected from eczema, atopic eczematous dermatitis, seborrheic dermatitis, contact dermatitis, irritant dermatitis, xerosis (dry skin), fungal infections including athlete's foot, yeast infections including diaper rash and vaginal itch, parasitic infections, parasitic infestations including scabies and lice, lichen planus, lichen simplex, lichen simplex chronicus, lichen sclerosis, itch secondary to medications, senile itch, uremia, idiopathic itch, itch associated with liver cirrhosis, itch associated with inflammation, itch associated with allergies, itch associated with cancer, itch associated with kidney disease, itch associated with haemodialysis, burns, scalds, sunburn, wound healing, insect bites, urticaria, sweat gland abnormalities, bullous pemphigoid, photodematoses, skin blisters, adult acne, chicken pox, seasonal allergy, summer seasonal recurrent dermatitis, prurigo nodularis, notalgia paresthetica and cutaneous T-cell lymphoma and dermatitis herpetiformis.

This invention is further illustrated by the following example which should not be construed as limiting. The contents of all references cited throughout this application, as well as the figures and table are incorporated herein by reference.

EXAMPLE

Materials and Method

Cloning and synthesis of recombinant human cysteine proteases S and K.

The genes encoding the human cysteine proteases S and K were expressed in E. coli in their inactive zymogen form, cleaved to their active enzyme form, and purified by filtration.

PAR activation observed by cytoplasmic calcium release—The four human PAR cDNAs were obtained from commercial sources and cloned into the pcDNA3.1(−) vector (INVITROGEN™ Inc.). HeLa cells were transfected with 10 μg of vector cDNA using Lipofectamine 2000 (INVITROGEN™ Inc.) and cultured for two days in 96-well glass bottom plates at 30,000 cells/well. Cells were loaded with Fura-2 as follows. The medium was aspirated and replaced with 100 μl of complete DMEM containing 2 μM Fura-2 (INVITROGEN™ Inc.) and kept at room temperature in the dark for 1 hr. The medium was again aspirated and each well received 90 μl of HEPES buffered saline (20 mM HEPES, 115 mM NaCl, 5.4 mM KCl, 2 mM $CaCl_2$, 0.8 mM $MgCl_2$, 13.8 mM glucose, pH 7.4). Plates were observed using a Zeiss Axiovert 200M microscope equipped with a filter wheel for monitoring excitation at 340 and 380 nm. Axiovision software, version 4.6 was used to analyze ratiometric calcium imaging of the cells. Ten μl of a 21 μM solution of recombinant human cathepsin S were applied approximately 20 seconds after the start of excitation. The final volume was 100 μl and the concentration of cathepsin S was 2.1 μM. Images were taken every 5 seconds, beginning at time zero, for 3 minutes. The software was used to analyze the 37 images taken during each 3-minute period.

Results

Figure 1:
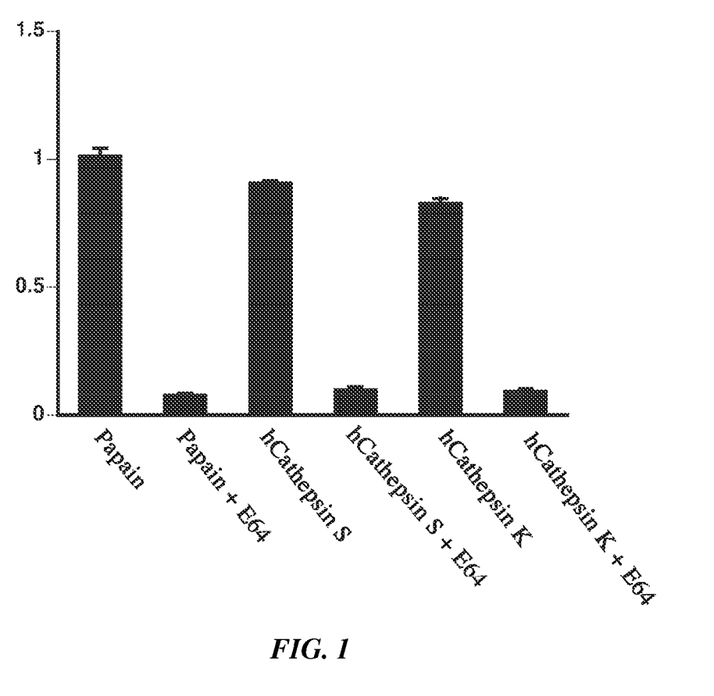
FIG. 1 shows a chromogenic substrate assay of human cathepsin S, human cathepsin K and papain. The concentrations of all the three proteases are at 0.84 µM and that of E64, a non-selective irreversible inhibitor of cysteine proteases, is at 2 µM DNA.

The inventors focused on human cathepsin S because it shares active site sequence homology with mucunain and is selectively up-regulated in human keratinocytes upon stimulation with interferon-gamma, consistent with a possible pruritic role in inflammatory skin disease (C. Shpacovitch et al., J. Leuk. Biology 83:1309-1322 (2008)). The purified cathepsin S and cathepsin K had protease activity as shown by their capacity to cleave the chromogenic substrate Z-Phe-Arg-pNA (FIG. 1). This activity was eliminated by the cysteine protease inhibitor E64, as shown in FIG. 1. Papain served as a positive control cysteine protease. The cathepsin S and K were further evaluated for their capacity to activate PAR receptors as noted below.

Figure 2:
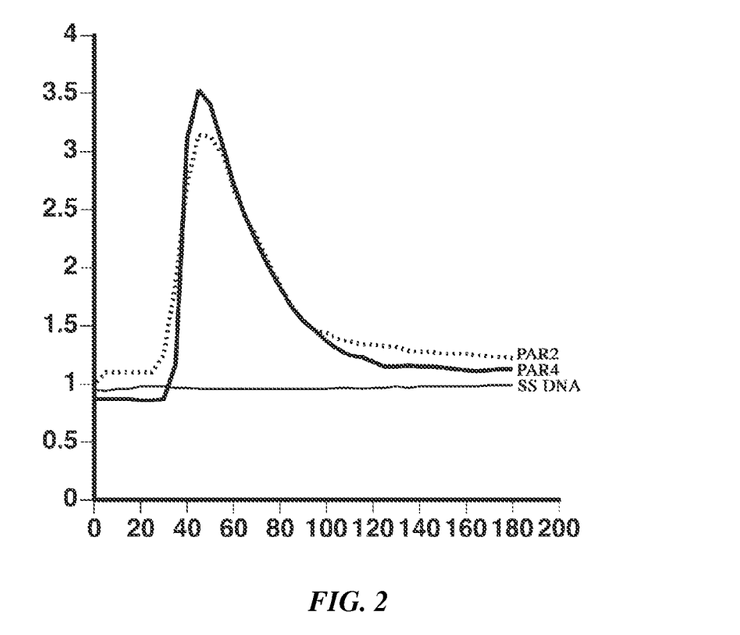
FIG. 2 shows human cathepsin S (2.1 µM) activation of HeLa cells transfected with plasmids encoding PAR2, PAR4, and, as a control, salmon sperm (SS) DNA. PAR1, PAR2+ E64 and PAR4+E64 gave activation similar to SS DNA.
Figure 3:
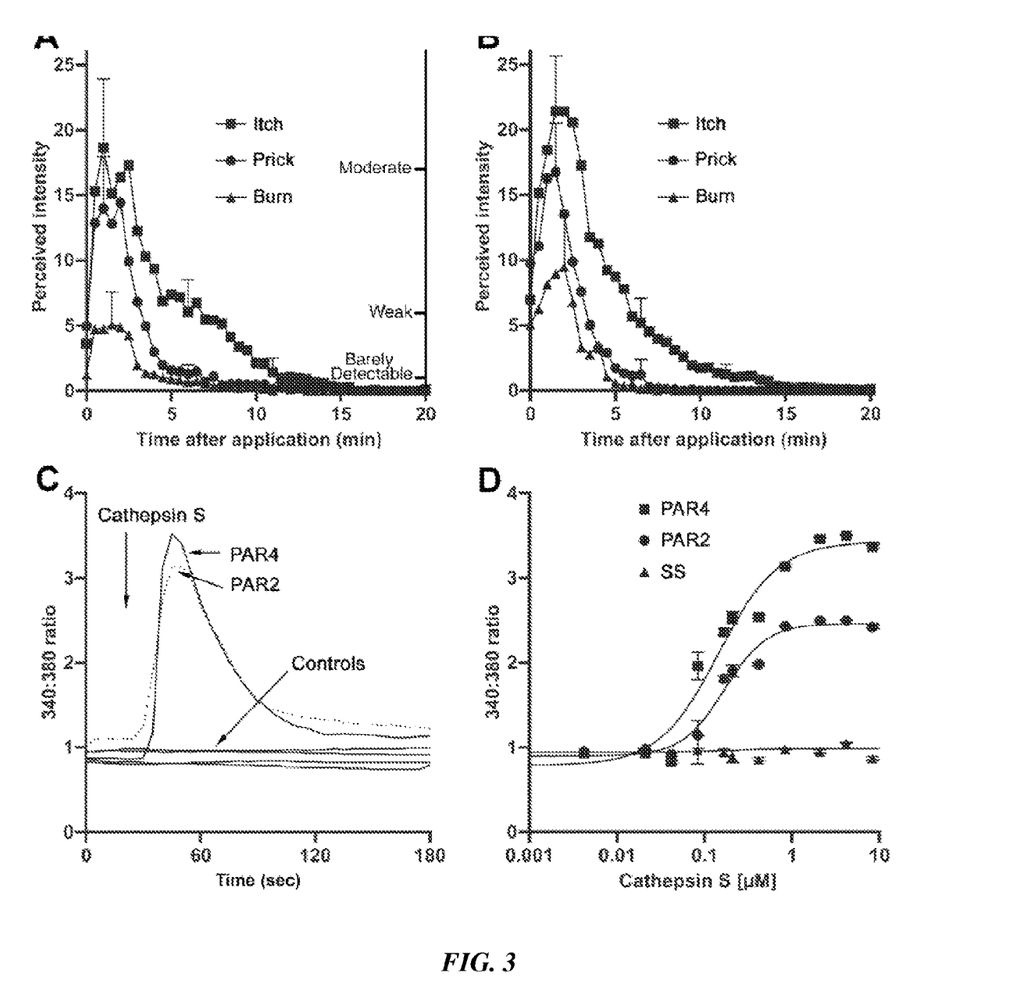
FIG. 3A shows the mean perceived intensity of itch and nociceptive sensations evoked by a single inactivated spicule reconstituted with recombinant human cathepsin S. Nine subjects were tested and mean±SE were plotted at 5 minutes intervals starting at the peak magnitude of the sensory quality.
FIG. 3B shows the mean perceived intensity of sensations evoked by a single spicule of native cowhage (same 9 subjects as in FIG. 3B).
FIG. 3C shows the single cell imaging of cathepsin S (2 µM) induced responses in HeLa cells transfected with PARs 2 and 4 as measured by ratiometric calcium imaging in cells loaded with fura-2. The responses to PAR 2 and 4 were blocked by the protease inhibitor E64 (10 µM) as a control). Other controls included vector alone and vector encoding the PAR1 receptor. Cathepsin S was added as indicated. The averages from at least three separate experiments were then combined +/−SD.
FIG. 3D shows the concentration—effect responses of cathepsin S in HeLa cells transiently transfected with PARs 2 and 4 as determined by ratiometric imaging. Salmon sperm (SS) DNA is used as control. The averages from at least three separate experiments were then combined +/−SD.

The inventors showed here that human cathepsin S is a ligand for protease-activated receptors 2 and 4. The effects of recombinant human cathepsin S, a cysteine protease, on PAR activation are shown in FIG. 2 and FIGS. 3C and 3D. Strong activation of PAR2 and PAR4, as determined by calcium flux demonstrated in the FIG. 2, occurred at a concentration of 30 nM. This concentration is at least ten-fold less than that needed for stimulation via mucunain. There was no activation of PAR1. Similar results were obtained with cathepsin K.

Recombinant cathepsin S also evokes itch in human volunteers. In this experiment, native itch-evoking spicules from the plant *Mucuna pruriens* were inactivated by autoclaving for 1 hour and reconstituted with recombinant cathepsin S. Typically, 50 mg of inactivated spicules were mixed with 0.4 ml of 1 mg of recombinant cathepsin S in 0.1M NaCl with 0.01 M L-cysteine in a 2 ml microfuge tube, vortexed, dried in a Speed-vac for 2 hours at room temperature, vortexed again and transferred to a new tube. This second vortex step allowed for precipitated salt to be separated from the spicules. These spicules were then considered 'reconstituted' with the cathepsin S. Individual spicules were then superficially inserted approximately 0.2 mm into the skin of volunteers who rated the subsequent itch as "very strong". The mean perceived intensity of itch and nociceptive sensation evoked by a single inactivated spicule reconstituted with cathepsin S on nine human volunteers is shown in FIG. 3A. The mean perceived intensity is similar with that for itch and nociceptive sensation evoked by a single spicule of native cowhage for the same nine volunteers. This indicates that the same pathway is being activated by cathepsin S and by the spicules from cowhage.

TABLE I

Cysteine protease inhibitors

E-64
U.S. Pat. No. 6,835,727 Cathepsin cysteine protease inhibitors
U.S. Pat. No. 7,279,478 Cathepsin cysteine protease inhibitors
U.S. Pat. No. 6,953,793 Substituted pyrazoles and methods of treatment with substituted pyrazoles
(WO/2005/066159) Cathepsin cysteine protease inhibitors
US 2007/0117785 Substituted pyrazoles and methods of treatment with substituted pyrazoles
Stefin A, stefin B, cystatin C
human testican-1
naphthalene endoperoxide (effective against Cathepsin B, L, S)
fluoromethyl ketone
heterocyclic oxygen-containing peptidomimetics
vinyl sulfones
pyrazole-based compounds such as 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine (JNJ 10329670)
RWJ-445380
Compounds I, II, and III, from Boehringer Ingelheim Pharmaceuticals
Leupeptin
chloroquine

```
                        SEQUENCE LISTING

<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Ser Leu Leu Arg Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Pro Gly Lys Phe
1               5
```

The inventors further studied the distribution and localization of cathepsin S in the epidermis of patients afflicted with cutaneous T-cell lymphoma, a known an itchy skin condition. They showed in a histopathologic image of a skin biopsy section of such a patient, that cathepsin S but not cathepsin O(cathepsin K), is detected (data not shown). Antibodies to cathepsin S and cathepsin O were incubated with frozen sections from a skin biopsy taken from lesional skin. The antibodies were detected using the VectaStain technique (Vector Laboratories, Burlingame, Calif.) and staining developed with DAB.

What is claimed is:

1. A method of preventing itch in a subject in need thereof, comprising administering to the subject a therapeutically effective amount of a cysteine protease inhibitor, wherein the inhibitor is an inhibitor of cathepsin S.

2. A method of treating itch in a subject in need thereof, comprising administering to the subject a therapeutically effective amount of a cysteine protease inhibitor, wherein the itch is not a symptom or sensation of psoriasis and atopic dermatitis, and wherein the inhibitor is an inhibitor of cathepsin S.

3. The method of claim 1, wherein the itch is non-histamine mediated.

4. The method of claim 1, wherein the cathepsin S inhibitor is 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine or derivatives thereof.

5. The method of claim 2, wherein the itch is non-histamine mediated.

6. The method of claim 2, wherein the cathepsin S inhibitor is 1-[3-[4-(6-Chloro-2,3-dihydro-3-methyl-2-oxo-1H-benzimidazol-1-yl)-1-piperidinyl]propyl]-4,5,6,7-tetrahydro-5-(methylsulfonyl)-3-[4-(trifluoromethyl)phenyl]-1H-pyrazolo[4,3-c]pyridine or derivatives thereof.

\* \* \* \* \*